(12) United States Patent
Zona

(10) Patent No.: US 8,544,351 B2
(45) Date of Patent: Oct. 1, 2013

(54) METHOD AND APPARATUS FOR CHARACTERIZING THE FLOWABILITY OF TONER PARTICLES

(75) Inventor: Michael F. Zona, Holley, NY (US)

(73) Assignee: Xerox Corporation, Norwalk, CT (US)

(*) Notice: Subject to any disclaimer, the term of this patent is extended or adjusted under 35 U.S.C. 154(b) by 514 days.

(21) Appl. No.: 12/791,901

(22) Filed: Jun. 2, 2010

(65) Prior Publication Data
US 2011/0296933 A1   Dec. 8, 2011

(51) Int. Cl.
*G01N 33/00* (2006.01)
*G01N 11/02* (2006.01)

(52) U.S. Cl.
USPC .......................................... 73/866; 73/54.35

(58) Field of Classification Search
USPC ............. 73/54.28, 54.31, 54.32, 54.34, 54.35
See application file for complete search history.

(56) References Cited

U.S. PATENT DOCUMENTS

| | | | | |
|---|---|---|---|---|
| 3,803,903 A | * | 4/1974 | Lin | 73/54.31 |
| 4,181,023 A | * | 1/1980 | Clamroth et al. | 73/866 |
| 4,484,468 A | * | 11/1984 | Gau et al. | 73/54.35 |
| 4,633,712 A | * | 1/1987 | Scieszka | 73/866 |
| 5,109,717 A | * | 5/1992 | Galetto et al. | 73/866 |
| 5,165,291 A | * | 11/1992 | Galetto et al. | 73/866 |
| 5,301,541 A | * | 4/1994 | Joseph et al. | 73/54.32 |
| 5,763,766 A | * | 6/1998 | Robinson | 73/54.33 |
| 5,847,294 A | | 12/1998 | Poole | |
| 5,959,222 A | | 9/1999 | Poole | |
| 5,987,970 A | * | 11/1999 | Ball | 73/54.28 |
| 6,065,330 A | * | 5/2000 | Freeman et al. | 73/54.28 |
| 6,158,293 A | | 12/2000 | Poole | |
| 6,528,222 B2 | * | 3/2003 | Kohtaki et al. | 430/108.21 |
| 6,874,353 B2 | * | 4/2005 | Johnson et al. | 73/54.28 |
| 7,939,234 B2 | * | 5/2011 | Matsumoto et al. | 430/111.35 |
| 2007/0107540 A1 | * | 5/2007 | Davies | 73/866 |
| 2009/0047043 A1 | * | 2/2009 | Dojo et al. | 399/252 |

OTHER PUBLICATIONS

J. Mellmann, "The transverse motion of solids in rotating cylinders—forms of motion and transition behavior," (2001), Powder Technology, 118, pp. 251-270.*

* cited by examiner

*Primary Examiner* — John Fitzgerald
(74) *Attorney, Agent, or Firm* — Fay Sharpe LLP

(57) ABSTRACT

Disclosed are methods and apparatuses for characterizing the flowability of a dry powder, and particularly for use with toner particles. The methods and apparatuses use an optionally transparent or semi-transparent cylindrical container. When the container is partially filled with dry powder, the dry powder is aerated and torque measurements are then taken while rotating the container to determine the flowability of the dry powder.

12 Claims, 4 Drawing Sheets

METHOD AND APPARATUS FOR CHARACTERIZING THE FLOWABILITY OF TONER PARTICLES

BACKGROUND

The present disclosure relates to methods and apparatuses useful in characterizing the flowability of a dry powder. In particular, the methods and apparatuses are useful in characterizing the flowability of toner particles.

A typical flexible electrophotographic imaging member belt comprises at least one photoconductive insulating layer. The imaging member is imaged by uniformly depositing an electrostatic charge on the imaging surface of the electrophotographic imaging member and then exposing the imaging member to a pattern of activating electromagnetic radiation, such as light, which selectively dissipates the charge in the illuminated areas of the imaging member to create an electrostatic latent image in the non-illuminated areas. This electrostatic latent image may then be developed to form a visible image by depositing finely divided electroscopic marking toner particles on the imaging member surface. The resulting visible image can then be transferred to a suitable receiving member or substrate, such as paper.

A two-component developer or a single-component developer may be used to develop the visible image. A two-component developer may be composed of a non-magnetic toner, i.e. a toner which does not contain magnetic particles, and a magnetic carrier. The toner particles are brought into frictional contact with the carrier particles and stick to the carrier particles electrostatically. The carrier particles are then adhered to a sleeve by magnetic force and transferred to a developing region. The toner particles are carried by the carrier particles to the developing region. In contrast, a single-component developer system uses only toner, and does not include a carrier. When the toner is not magnetic, the single-component developer system is known as a non-magnetic, single-component development (NMSCD) system.

Flowability is a measure of the ease with which a loose particulate solid flows. Flowability is critical to the performance of an imaging member. In particular, toner particles of a low flowability toner tend to agglomerate. Agglomeration may lead to the visible image not being an accurate representation of the electrostatic image, with areas of the substrate receiving too much or too little toner.

Methods for measuring flowability in a two-component development system include cohesion testing, Freeman FT4 testing, and angle of repose. In cohesion testing, a plurality of mesh screens with different sized openings is arranged in a vertical stack with the screen having the largest sized openings at the top. An aerated toner is poured into the top screen. After a fixed period of time, the amount of toner in the screen with the smallest sized openings, i.e. the bottom screen, is measured. A greater mass in the bottom screen correlates to a better flowability.

In Freeman FT4 testing, a sample of toner is compressed by a known force to determine how much the volume of the toner is reduced. A lower compressibility correlates to a better flowability.

The angle of repose can be determined by pouring an aerated toner sample into a funnel and measuring the angle of the pile of toner created under the funnel. A lower angle correlates to a better flowability.

The three tests described above can be used to characterize flowability in a two-component system. However, the results of these tests do not correlate well with the flow performance observed in NMSCD systems. It would be desirable to develop methods for characterizing the flowability of a toner in a NMSCD system.

BRIEF DESCRIPTION

The present application discloses, in various embodiments, methods and apparatuses for characterizing the flowability of a toner. Generally, the methods include rotating a cylinder containing a sample of the toner while measuring torque.

Disclosed in embodiments are processes for measuring flowability of toner particles, comprising: introducing a sample of toner particles to a cylindrical container having a central axis; rotating the cylindrical container about the central axis at a first speed to aerate the toner particles; and rotating the cylindrical container about the central axis at a second speed while measuring the torque of the cylindrical container; wherein the first speed is greater than the second speed.

The cylindrical container can be rotated clockwise and counterclockwise to aerate the toner particles. The torque of the cylindrical container can be measured for about 5 to about 10 revolutions. A sidewall of the cylindrical container may be transparent or semi-transparent.

The process may further comprise measuring torque while the cylindrical container is rotated at the first speed. Alternatively, the process may further comprise determining the time required to aerate the toner particles using measurements collected during rotation at the first speed. The process could further comprise calculating the average torque. The process might also further comprise determining the time between peaks in the torque measurements.

The first speed may be from about 80 to about 200 revolutions per minute. The second speed may be from about 30 to about 80 revolutions per minute.

Also disclosed in embodiments is an apparatus for measuring the flowability of a dry powder, comprising: a first shaft, a second shaft, and a cylindrical container for holding the dry powder, wherein the cylindrical container is located between the first shaft and the second shaft, and wherein the first shaft, the cylindrical container, and the second shaft define a central axis; a motor configured to rotate the second shaft about the central axis; and a torque transducer mounted to the second shaft to measure variations in torque caused by movement of the dry powder within the cylindrical container.

In embodiments, the first shaft comprises a first grip, the second shaft comprises a second grip, and the cylindrical container is supported by the first and second grips.

A spring may be used to bias the first grip towards the cylindrical container and the second grip.

A computer may also be part of the apparatus for controlling the motor and receiving data from the torque transducer.

The apparatus may further comprise a base, a first support beam, and a second support beam, the two support beams extending from the base, the first shaft being mounted on the first support beam, the second shaft and the motor being mounted on the second support beam.

The cylindrical container generally has a diameter and a height, the height being greater than the diameter. A sidewall of the cylindrical container may be at least semi-transparent.

Also disclosed is a process for measuring the flowability of a toner, comprising: introducing a toner sample to a cylindrical container having a central axis; rotating the cylindrical container about the central axis at a first speed to aerate the toner sample; and rotating the cylindrical container about the central axis at a second speed while measuring the torque of the cylindrical container; wherein the first speed is greater than the second speed.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
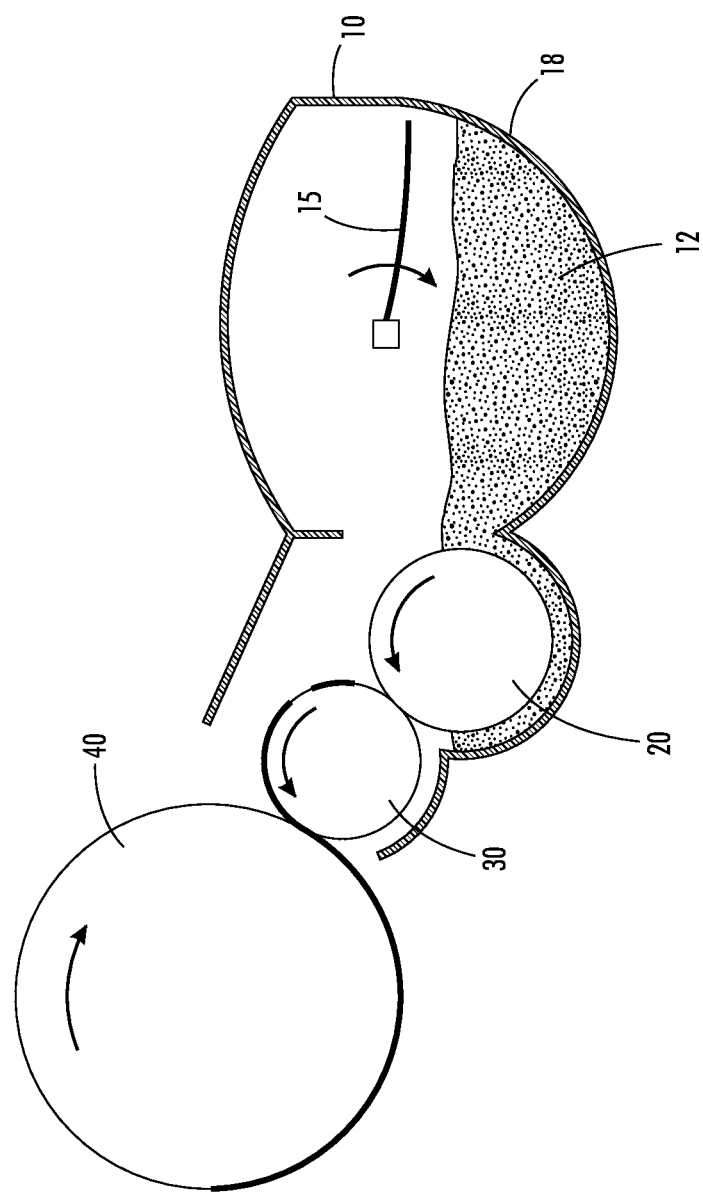
FIG. 1 is a schematic view of the typical components of a NMSCDS housing.

A more complete understanding of the components, processes, and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10".

The present disclosure relates to processes for measuring the flowability of a toner. The processes include introducing a toner sample to a cylindrical container having a central axis. The cylindrical container is rotated about the central axis at a first speed to aerate the toner sample. The cylindrical container is then rotated about the central axis at a second speed while measuring the torque of the cylindrical container. The first speed is greater than the second speed.

The present disclosure also relates to an apparatus for measuring the flowability of a particulate. The apparatus comprises a shaft, a cylindrical container for holding a particulate sample, and a torque transducer. A circumferential sidewall of the cylindrical container is transparent or semitransparent. The cylindrical container is directly or indirectly connected to the shaft.

Also disclosed is a process for measuring the flowability of a toner. The process comprises introducing a toner sample to a cylindrical container having a central axis. The cylindrical container is rotated about the central axis at a first speed to aerate the toner sample. Then, the cylindrical container is rotated about the central axis at a second speed while measuring the torque of the cylindrical container. The first speed is greater than the second speed.

In FIG. 1, a schematic view of a typical non-magnetic single component development (NMSCD) system is shown. A toner housing 10 contains a toner paddle 15 and a toner sump 18. Toner 12 is stored in the toner sump. The toner paddle rotates within the housing 10 to both aerate the toner and to push toner 12 from the toner sump 18 to a donor roll 20. It should be noted that the donor roll 20 is located at a higher elevation compared to the toner sump 18, to prevent toner from escaping the sump. The donor roll 20 feeds toner to a developer roll 30, which subsequently delivers the toner to a photoreceptor 40.

Factors influencing flowability include particle shape, particle size, additive types, additive size, and adhesion of the additive to the particle. These factors also influence the overall function of the toner, i.e. toner charge to mass ratio (Q/m), mass on roll (MOR), etc. However, conventional flowability tests do not accurately predict how a toner will perform in a NMSCD system.

Figure 2:
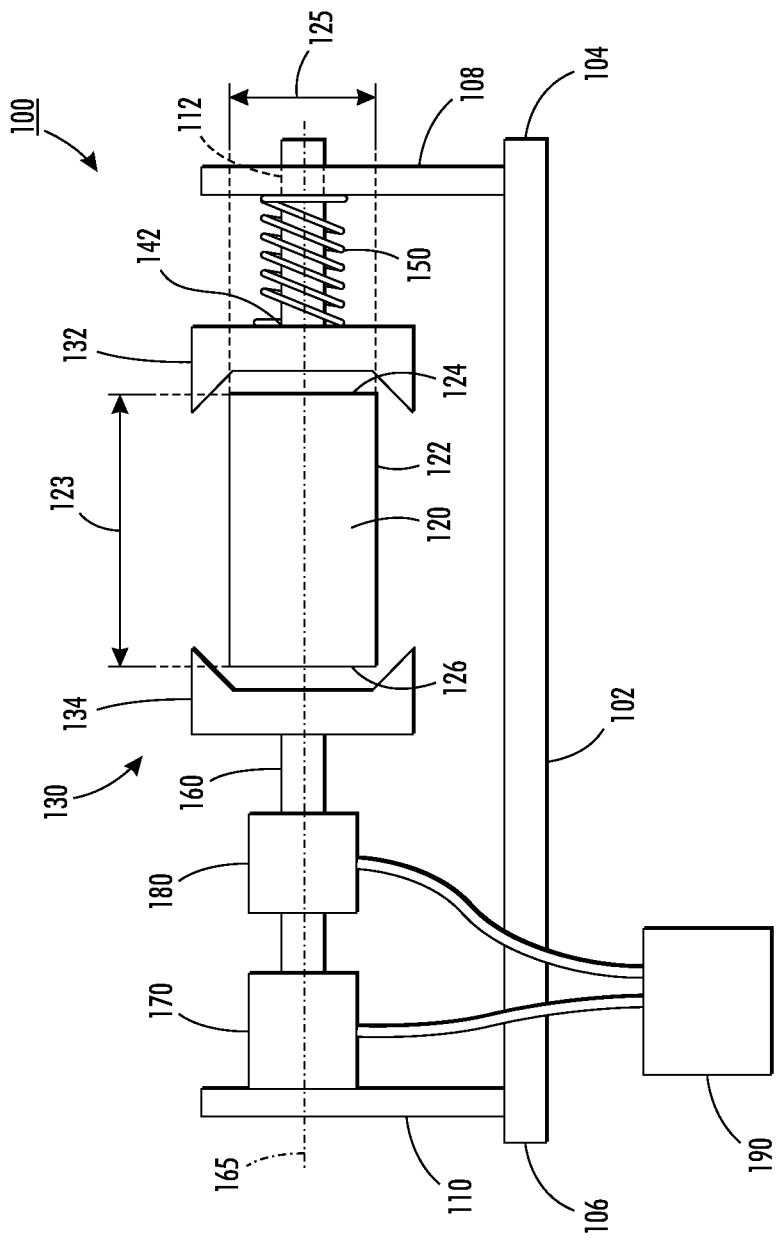
FIG. 2 is a schematic view of an embodiment of an apparatus of the present disclosure.

FIG. 2 depicts an exemplary apparatus 100 for determining the flowability of dry powders or particulates. The apparatus includes a base 102 having a first end 104 and a second end 106. A first support beam 108 rises from the base 102 at the first end 104, and a second support beam 110 rises from the base 102 at the second end 106. The various components of the apparatus are generally mounted on one of the two support beams 108, 110. The two support beams are generally perpendicular to the base 102.

A cylindrical container 120 is provided to hold a particulate sample. The container 120 includes a sidewall 122 and two ends 124, 126. The sidewall 122 may be transparent or semitransparent, to allow an operator to visually monitor the behavior of the particulate. The container has a height 123 which is greater than its diameter 125. In particular embodiments, the ratio of the height to the diameter is at least 2:1. In some embodiments, the cylinder 120 contains visual markers, such as lines or dots, which aid in identifying the degree to which the cylinder has been rotated.

The cylinder 120 is placed into a cylinder locator 130. The cylinder locator 130 has a first grip 132 and a second grip 134. The first grip 132 is attached to one end 142 of a first shaft 140. A spring 150 is located around the first shaft 140 between the first grip 132 and the support beam 108, and biases the first grip 132 towards the cylindrical container 120. The spring, however, is not connected to first grip 132. As is known in the art, the first shaft 140 can either be constructed to shorten in length as the first grip 132 is pushed towards the support beam 108, or the first shaft 140 may pass through a hole 112 in support beam 108. The second grip 134 is connected to a second shaft 160. The second shaft 160 is of a fixed length and does not change position. Together, the first shaft 140 and the second shaft 160 define a central axis 165 around which the cylinder 120 will rotate. The cylinder 120 is coaxial with the central axis as well.

A motor 170 is mounted on the second end 106 of the apparatus to drive the rotation of the second shaft 160. The motor 170 causes the second shaft 160 to rotate. First shaft 140 is also mounted so as to be able to freely rotate along with the cylinder 120.

A torque transducer 180 is also mounted on the second shaft 160. The torque transducer is used to measure the rotational torque on the second shaft 160.

A computer 190 can be connected to both the motor 170 and the torque transducer 180. The computer 190 may be used to power and/or control the motor 170. The computer 190 may also be used to analyze and/or display torque data based on the electrical signal from the torque transducer 180.

The apparatus 100 is used to practice the methods of the present disclosure. Generally speaking, a fixed amount of toner is placed in the cylindrical container and the torque is monitored while the cylinder is rotated. The amplitude of the torque provides a quantitative measure of the flowability of the toner. A poor flowing toner will have a greater variation in the amplitude of the torque than a well flowing toner. High flowability toners should not exhibit high amplitude peaks because high flowability toner particles tend to remain at the bottom of the cylinder during rotation. On the other hand, low flowability toner particles should tend to rotate with the cylinder until a threshold angle of rotation, or avalanche point, is reached. At the avalanche point, aggregated particles fall back down to the bottom of the cylinder.

Figure 3A:
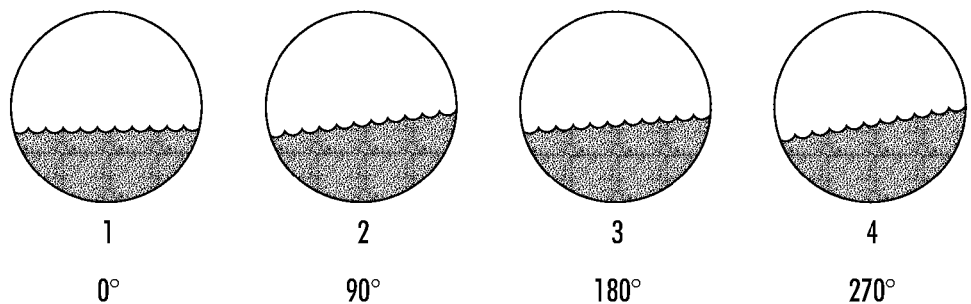
FIG. 3A shows four side view illustrations of a high flowability toner in a cylinder at various angles of rotation.
Figure 3B:
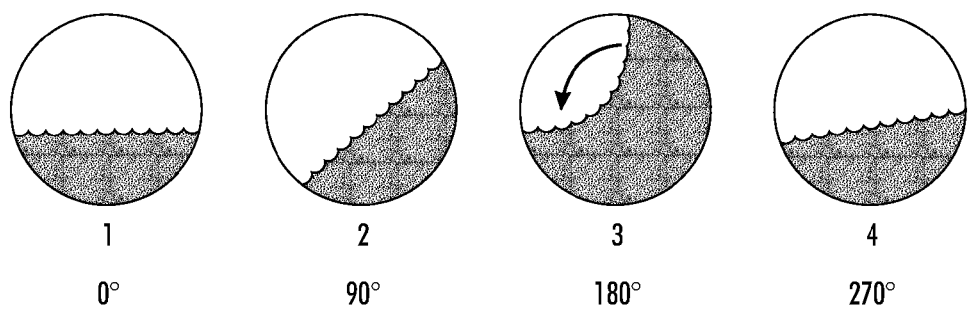
FIG. 3B shows four side view illustrations of a low flowability toner in a cylinder at various angles of rotation.

FIGS. 3A and 3B are various views from the first end 104 of the apparatus 100. FIG. 3A shows the cylinder at various angles of rotation for a high flowability toner, while FIG. 3B shows the same angles for a low flowability toner, with the angles being measured for counter-clockwise rotation. As seen in FIG. 3A, as the cylinder is rotated, the high flowability toner continually flows down to the bottom of the cylinder, as seen by its relatively constant flatness. In FIG. 3B, the low flowability toner tends to aggregate and adhere both to other toner particles and to the sidewall of the cylinder. Near the 180° angle of rotation, i.e. after about half of one revolution, the toner is nearing the avalanche point. At a rotational angle of 270°, the toner particles have fallen down to the bottom of the cylinder, i.e. the "avalanche" has occurred. This difference in the behavior of the toner creates variations in torque, and that information can be captured by the torque transducer. This behavior can also be visually witnessed through the transparent/semi-transparent cylindrical container.

Initially, the cylindrical container 110 is rotated at a relatively high rotational speed. This first speed or high speed may be within a range of from about 80 to about 200 rotations per minute (rpm). This initial high speed rotation helps to aerate the toner sample prior to measuring its flowability. In some embodiments, aeration is performed by rotating the cylinder in both a counterclockwise and clockwise direction, relative to the central axis 165 when viewed from the first end 104 of the apparatus. In such embodiments, the rotation may begin in either direction, then be reversed to rotate in the other direction. Aeration is critical in simulating flowability in a NMSCD system because the toner in such systems is aerated by the toner paddle. Aeration prevents agglomeration and breaks up clumps of toner, so that the toner in the apparatus will be in the same condition and act the same way as in a printing system. In addition, aeration stabilizes the toner sample into a known condition, so that different toner samples can be compared to each other for flowability, without the worry that some samples were settled more than others. In some embodiments, the computer 190 measures the time required to aerate a toner sample based on the data obtained from the torque transducer 180. This calculation may be based on the average torque of the sample during the aeration step of the procedure. As the sample gets more aerated, the average torque per revolution will stabilize to some fixed value. When this plateau in torque occurs, one can have confidence the sample is fully aerated. A shorter time to aerate indicates better flowability.

Next, the rotational speed is reduced to a second speed. In other words, the first speed is greater than the second speed. The second speed may be from about 30 to about 80 rpm. The rotational torque is monitored during this second speed.

In some embodiments, the torque is monitored for from about five to about ten cylinder revolutions. The data collected by the computer 190 can then be analyzed to produce a measurement of the flowability of the toner.

The amplitude of the rotational torque as a function of time, or as a function of the number of cylinder rotations, can visually illustrate the results. Alternatively, the average torque can be calculated, or the time between peaks during each cycle, may be used to calculate the weight or volume of toner that moves with the cylinder instead of remaining at the bottom. The peak-to-peak time may be used to determine the angle at which the toner falls back to the bottom of the cylinder. All of these measurements can be used to quantify the flowability of the toner in the cylinder.

Figure 4:
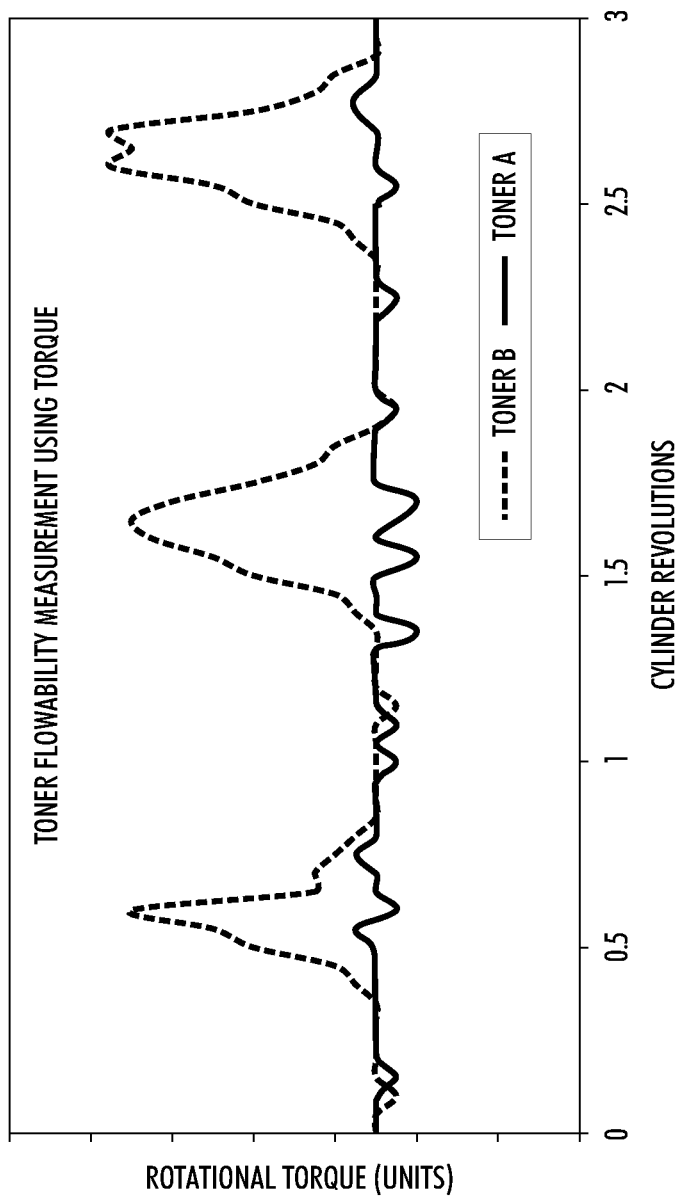
FIG. 4 is a graph of torque as a function of cylinder revolutions for a toner having high flowability and a toner having low flowability.

FIG. 4 is a graph of rotational torque as a function of cylinder revolutions for both a high flowability toner (Toner A) and a low flowability toner (Toner B). The high flowability toner curve is relatively flat because the toner stays at the bottom of the rotating cylindrical container. Thus, there is no significant avalanching and hence, little impact to the torque required to rotate the cylinder. The low flowability toner exhibits high peaks slightly past 0.5, 1.5, and 2.5 rotations. These peaks are due to the higher torque required by the motor to maintain constant RPM, due to the avalanching of the toner in the cylinder. Since 0.5, 1.5, and 2.5 rotations each correspond to a rotational angle of 180°, the avalanche point is at angle of rotation slightly greater than 180°.

While particular embodiments have been described, alternatives, modifications, variations, improvements, and substantial equivalents that are or may be presently unforeseen may arise to applicants or other skilled in the art. Accordingly, the appended claims as filed and as they are amended are intended to embrace all such alternatives, modifications, variations, improvements, and substantial equivalents.

What is claimed is:

1. A process for measuring flowability of toner particles, comprising:
    introducing a sample of toner particles to a cylindrical container having a central axis;
    rotating the cylindrical container about the central axis at a first speed to fully aerate the toner particles; and subsequently
    rotating the cylindrical container about the central axis at a second speed while measuring the torque of the cylindrical container to measure the flowability of the toner particles;
    wherein the first speed is greater than the second speed.

2. The process of claim 1, wherein the cylindrical container is rotated clockwise and counterclockwise to fully aerate the toner particles.

3. The process of claim 1, wherein the torque of the cylindrical container is measured for from about 5 to about 10 revolutions.

4. The process of claim 1, wherein a sidewall of the cylindrical container is transparent or semi-transparent.

5. The process of claim 1, further comprising calculating the average torque.

6. The process of claim 1, further comprising determining the time between peaks in the torque measurements.

7. The process of claim 1, wherein the first speed is from about 80 to about 200 revolutions per minute.

8. The process of claim 1, wherein the second speed is from about 30 to about 80 revolutions per minute.

9. The process of claim 1, further comprising measuring torque while the cylindrical container is rotated at the first speed.

10. The process of claim 9, further comprising determining the time required to fully aerate the toner particles using measurements collected during rotation at the first speed.

11. A process for measuring the flowability of a toner, comprising:
   introducing a toner sample to a cylindrical container having a central axis;
   rotating the cylindrical container about the central axis clockwise and counterclockwise at a first speed to fully aerate the toner sample; and subsequently
   rotating the cylindrical container about the central axis at a second speed while measuring the torque of the cylindrical container to determine the flowability of the toner;
   wherein the first speed is greater than the second speed.

12. The process of claim 11, wherein the torque of the cylindrical container is measured for from about 5 to about 10 revolutions.

* * * * *